United States Patent [19]
Ageishi et al.

[11] Patent Number: 5,880,310
[45] Date of Patent: Mar. 9, 1999

[54] PROCESS FOR PRODUCING PLASTICIZER ESTERS

[75] Inventors: Kuniaki Ageishi; Tadayoshi Takefumi; Tsutomu Numoto; Tsuguji Kawabata; Etsuo Urabe, all of Kurashiki, Japan

[73] Assignee: Mitsubishi Gas Chemical Company, Inc., Tokyo, Japan

[21] Appl. No.: 65,233

[22] Filed: Apr. 23, 1998

[30] Foreign Application Priority Data

May 21, 1997 [JP] Japan ................................ 9-131035
May 21, 1997 [JP] Japan ................................ 9-131036
Jun. 23, 1997 [JP] Japan ................................ 9-165867

[51] Int. Cl.$^6$ .................................................. C07C 67/48
[52] U.S. Cl. .............................................. 560/99; 560/78
[58] Field of Search ......................................... 560/99, 78

[56] References Cited

U.S. PATENT DOCUMENTS 4,284,793  8/1981  Sagara et al. .............................. 560/78
4,334,080  6/1982  Koichi et al. .............................. 560/78

FOREIGN PATENT DOCUMENTS 56-110650  9/1981  Japan .
56-39296   9/1981  Japan .
15656636   4/1980  United Kingdom .

Primary Examiner—Samuel Barts
Attorney, Agent, or Firm—Wenderoth, Lind & Ponack, L.L.P.

[57] ABSTRACT

Provided is a process for producing a plasticizer ester characterized by previously removing dissolved oxygen in a starting alcohol, and then subjecting an organic acid or its anhydride and the alcohol to an esterification reaction in the presence of an organic metal compound catalyst, which process can substantially reduce formation of coloring impurities and can easily provide a plasticizer ester having a low degree of coloring.

Further, a plasticizer ester having a high volume resistivity can easily be obtained by adding an alkaline aqueous solution to a reaction product obtained by an esterification reaction to conduct neutralization of an unreacted acid and hydrolysis of the catalyst, further blowing a carbon dioxide gas to convert the residual alkali into a carbonate, recovering an excess alcohol, and then conducting purification through finefiltration using a filter aid or further in combination with adsorption treatment.

11 Claims, No Drawings

PROCESS FOR PRODUCING PLASTICIZER ESTERS

BACKGROUND OF THE INVENTION

1. Field of the Invention

The present invention relates to a process for producing plasticizer esters which are used well in various plastics including a vinyl chloride resin. More specifically, the present invention relates to a process for producing a high-quality plasticizer ester required for plasticized soft vinyl chloride which is widely used in an equipment for medical care, a wire cable, an insulating material and the like from an organic acid or its anhydride and an alcohol.

2. Description of the Prior Art

Plasticized soft vinyl chloride which is widely used in the medical field, the electric field, the electronic field and the like requires a high-quality plasticizer ester. For example, a plasticizer free from toxic coloring impurities, namely, a plasticizer ester having a low degree of coloring is required in the medical field; and a plasticizer ester having a high volume resistivity is required in the electric field.

The coloring impurities in the plasticizer are divided into those derived from starting materials and those formed during the production step. With respect to impurities in starting materials, for example, aldehydes in an alcohol, unsaturated compounds, sulfur compounds and the like, or materials from an acid source, for example, quinone substances in phthalic anhydride, a purification technique for removing these impurities has been developed, and impurities of starting materials have been, therefore, considerably improved. However, esters are different at times in a degree of coloring thereof depending on esterification reaction conditions even starting from the same starting materials.

As a method for forming a plasticizer ester having a low degree of discoloring, the following methods are known.

(1) A method in which when monoesterification is conducted by the reaction of an organic acid and an alcohol under normal pressure, a predetermined amount of water is added to a reaction vessel to form a state where a surface of a reaction solution is coated with a water vapor, whereby oxygen in air is prevented from being brought into contact with the reaction solution to improve the hue (Japanese Patent Laid-Open No. 113,814/1976), (2) a method for producing an plasticizer ester having quite a low degree of coloring by causing a bisulfite to exist in a reaction system (Japanese Patent Laid-Open No. 41,742/1976), (3) a method for producing a plasticizer ester having a low degree of coloring in which oxalic acid is added when subjecting an organic acid or its anhydride and an alcohol to an esterification reaction in the presence of an organic metal compound catalyst (British Patent No. 1,565,663), (4) a method in which a carboxylic acid ester is treated with an oxidizing agent such as hydrogen peroxide, sodium chlorite or the like and then with an alkaline aqueous solution, and the thus-treated product is washed with water, and further treated with a reducing agent such as sodium borohydride, hypophosphorous acid or the like for decoloration (Japanese Patent Laid-Open No. 22,618/1980), (5) a method in which a carboxylic acid is reacted with an alcohol, and the resulting product is purified by passing ozonization air therethrough under specific conditions (Japanese Patent Laid-Open No. 39,296/1981), and (6) a method in which an ester is continuously decolored in the presence of a Pd catalyst under hydrogenation conditions (Japanese Patent Laid-Open No. 110,650/1981).

Meanwhile, as a method for producing a plasticizer ester having a high volume resistivity, the following methods are known. (7) A method in which an esterification reaction product is heat-treated with a solid alkali such as sodium carbonate in the absence of water, and a reaction product is adsorbed with an adsorbent such as activated china clay (Japanese Patent Laid-Open Nos. 76,517/1979, 27,518/1979 and 27,519/1979), (8) a method in which a crude ester obtained by an esterification reaction is treated with oxidized magnesium silicate (British Patent No. 1,096,917 and the like), (9) a method in which the treatment is conducted with an absorbent such as magnesium oxide, activated carbon or the like (Japanese Patent Laid-Open No. 267,341/1987), and (10) a method in which an organic metal catalyst in an esterification reaction solution is hydrolyzed, neutralized with an alkali, and washed with water, an excess alcohol is recovered, and the resulting ester is treated with an adsorbent such as activated carbon or activated china clay (Japanese Patent Laid-Open No. 130,937/1980 and the like).

SUMMARY OF THE INVENTION

In any of the above-mentioned methods (1) to (6) by which to obtain a plasticizer ester having a low degree of coloring, except the method (1) which provides the state where the surface of the reaction solution is coated with the water vapor, an additive, a catalyst or the like has to be used. The method (1) in which the surface of the reaction solution is coated with the water vapor provides a low effect. In the methods (2) to (6) using the additive, the catalyst or the like, the procedure is intricate, and its cost is high.

A first object of the present invention is to provide a process for producing plasticizer esters having a low degree of coloring through a simple procedure industrially advantageously without using the additive, the catalyst or the like.

The present inventor has assiduously conducted investigations to achieve the first object, and has consequently found that the degree of coloring of the plasticizer ester is remarkably reduced by conducting the deoxidation treatment in the step of feeding starting materials before the esterification reaction.

That is, the first invention is a process for producing plasticizer esters, which comprises previously removing dissolved oxygen in a starting alcohol, and then subjecting an organic acid or its anhydride and the alcohol to an esterification reaction in the presence of an organic metal compound catalyst.

Further, a plasticizer ester is produced by the reaction of an organic acid or its anhydride with an alcohol in the presence of an acid catalyst. Purification of a crude ester is important to obtain a plasticizer ester having a high volume resistivity in the electric field.

In all of the methods (7) to (10) for obtaining the plasticizer ester having the high volume resistivity, the treatment is conducted using the adsorbent. In order to provide the high volume resistivity, a large amount of the adsorbent has to be used. Since the adsorbent is costly and hardly reused, this method is uneconomical. Further, in the case of the continuous adsorption, there is a problem of a pressure loss; an adsorption vessel is needed in the batch-wise system, and its procedure is intricate.

The second object of the present invention is to provide a process for producing a plasticizer ester having an excellent volume resistivity industrially advantageously.

The present inventor has assiduously conducted investigations to achieve the second object, and has consequently found that a plasticizer ester having an excellent volume resistivity can easily be produced by subjecting an organic acid or its anhydride and an alcohol to an esterification reaction, blowing a carbon dioxide gas into the resulting crude ester to convert the residual alkali into a carbonate, recovering an excess alcohol, and then conducting finefiltration using a filter aid.

That is, the second invention is a process for producing a plasticizer ester, which comprises subjecting an organic acid or its anhydride and an alcohol to an esterification reaction in the presence of an organic metal compound catalyst, adding an alkaline aqueous solution to the resulting reaction product to conduct neutralization of an unreacted acid and hydrolysis of the catalyst, blowing a carbon dioxide gas to convert the residual alkali into a carbonate, recovering an excess alcohol, and then conducting finefiltration using a filter aid.

DETAILED DESCRIPTION OF THE INVENTION

As the organic metal compound catalyst to be used in the esterification reaction in the present invention, an alkyl titanate such as tetraisopropyl titanate, tetra-n-butyl titanate or tetra-2-ethylhexyl titanate, and an organic tin compound such as tin tetraethylate or butyltin maleate that exhibit a catalytic activity at an esterification reaction temperature are preferably used.

Examples of the organic acid or its anhydride to be used in the esterification reaction include aromatic monocarboxylic acids typified by benzoic acid and toluic acid; polybasic aromatic carboxylic acids or anhydrides thereof, such as phthalic acid, phthalic anhydride, isophthalic acid, terephthalic acid, trimesic acid, trimellitic acid, trimellitic anhydride, pyromellitic acid, pyromellitic anhydride, benzophenonetetracarboxylic acid and benzophenonetetracarboxylic anhydride; polybasic aliphatic carboxylic acids such as adipic acid, sebasic acid and azelaic acid; polybasic unsaturated aliphatic carboxylic acids such as maleic acid and fumaric acid; and aliphatic monocarboxylic acids such as oleic acid and stearic acid.

Examples of the alcohol to be used in the esterification reaction include saturated monohydric aliphatic alcohols such as methanol, ethanol, propanol, isopropanol, butanol, isobutanol, sec-butanol, heptanol, octanol, 2-ethylhexanol, isooctanol, isononyl alcohol formed by an oxo reaction of a butene dimer, decanol, isodecyl alcohol formed by an oxo reaction of a propylene dimer, undecanol and tridecanol; and polyhydric aliphatic alcohols such as ethylene glycol, propylene glycol and diethylene glycol. These alcohols can also be used in combination as required.

The esterification reaction is usually conducted by adding an alcohol which has been deoxidized to an organic acid or its anhydride, and reacting the mixture at from 150° C. to 220° C. for from 3 to 4 hours in the presence of an organic metal compound catalyst in an inert gas atmosphere while removing water formed outside the system. An alkaline aqueous solution is added to the resulting reaction solution to conduct neutralization of an unreacted acid and hydrolysis of the catalyst, and a carbon dioxide gas is then blown to convert the residual alkali into a carbonate. An excess alcohol is recovered, and the resulting product is then purified to obtain a plasticizer. In order to facilitate the ester purification after the reaction, it is advisable to set a reactivity at 99.8% or more as much as possible.

The first invention for obtaining the ester plasticizer having a low degree of coloring is characterized in that formation of coloring impurities which is accelerated by incorporating oxygen during the esterification reaction can substantially be reduced by previously removing dissolved oxygen in the starting alcohol whereby the plasticizer ester having the low degree of coloring can be produced.

As a method for previously removing dissolved oxygen in the starting alcohol, for example, (1) a method in which bubbling is conducted with an oxygen-free inert gas, (2) a method in which deoxidation is conducted under reduced pressure, and (3) a method in which deoxidation is conducted through distillation are mentioned. Any of these methods for removing oxygen is available in the present invention.

When the bubbling is conducted with an inert gas, it is advisable that an amount of an inert gas such as nitrogen is 20N liters or more per liter of an alcohol. When the amount of the inert gas is less than the above-mentioned, a time required for the deoxidation treatment is prolonged.

When the deoxidation is conducted at reduced pressure, the pressure varies depending on the type of the alcohol, and a pressure and a temperature suitable for preventing evaporation of an alcohol have to be selected.

The deoxidation temperature varies depending on the type of the alcohol. It is generally between 30° and 100° C. When it is less than 30° C., a deoxidation treatment for a long period of time is required. Since an alcohol is evaporated at a temperature of more than 100° C., an equipment for recovering an alcohol evaporated is needed, and it is uneconomical.

The formation of coloring impurities in the esterification reaction can substantially be reduced by previously removing dissolved oxygen in the starting alcohol, and the plasticizer ester having the low degree of coloring can easily be obtained.

According to the first invention, the plasticizer ester having the low degree of coloring can be obtained through a simple procedure without using an additive, a catalyst or the like.

In the second invention for obtaining a plasticizer ester having an excellent volume resistivity, the purification is conducted through finefiltration using the filter aid to obtain a plasticizer ester from which impurities that decrease properties as a plasticizer, for example, a half ester salt, a carbonate, titanium oxide and the like are removed, of which the hue is improved and which has an excellent volume resistivity.

As the filter aid to be used in the finefiltration, a filter aid produced from diatomaceous earth which is generally marketed [for example, Radiolite (made by Showa Kagaku Kogyo K. K.) and Celite (made by Johns Manville Sales Corp.)], a filter aid produced from perlite [for example, Topco Perlite (made by Showa Kagaku Kogyo K. K.) and Dicalite Perlite (made by Dicalite Orient K. K.) and the like are mentioned.

With respect to the filter aid, an optimum filter aid can be selected by the use of a mixture of filter aids having a different particle size or a combination with the other type of the filter aid. However, in order to conduct finefiltration, a filter aid having a particle size of 5 microns or less has to occupy 20% or more of the total ratio. It is preferable that this filter aid occupies 30% or more of the total ratio.

The amount of the filter aid is between 1 kg to 5 kg, preferably between 2 and 4 kg per $m^2$ of the filtration area. When the amount of the filter aid is too small, the filtration effect is decreased, making it impossible to obtain a high volume resistivity. Even when the amount of the aid is too large, the volume resistivity remains unchanged, and it does not become economically advantageous.

Since the filter aid containing large amounts of fine particles is used for finefiltration in the second invention, the filtration rate is decreased, but it is possible to jointly use a filter aid having a high filtration rate depending on the range of the volume resistivity required. In either case, however, the filtration rate is 10 liters/min or less, preferably between 3 and 7 liters/min per m² of the filtration area.

In the second invention, it is advisable to conduct purification through a combination of finefiltration using a filter aid and adsorption treatment for obtaining a plasticizer ester having a better volume resistivity.

Examples of the adsorbent to be used in the adsorption-treatment include activated alumina, activated china clay, activated carbon, magnesium oxide, aluminum oxide and silicon oxide. These may be used either singly or in combination.

In general, it is advisable that the amount of the adsorbent is between 0.1 and 1% by weight based on the weight of a crude ester. When it is smaller than this range, the adsorption effect is low, and no high volume resistivity can be obtained. Further, even when it is larger than this range, the effect of improving the quality is low, and it is thus uneconomical.

A filtration method includes a precoating method in which a slurry of a filter aid is previously filtered to form a cake layer of the filter aid on a surface of a filter medium, and a slurry of a dope is filtered through this filter medium, or a body feeding method in which an appropriate amount of a filter aid is incorporated into a slurry dope for filtration. Meanwhile, an adsorption method includes a method in which an adsorbent is added to a solution to conduct adsorption through stirring, namely, a method of adsorption through contact filtration, or a method in which an adsorbent is filled, and the layer is adsorped through a solution, namely a solid-phase adsorption method. In the present invention, both of these filtration methods are available.

With respect to the combination of adsorption treatment and finefiltration, there are, for example, (i) a method in which adsorption and filtration are conducted simultaneously, (ii) a method in which filtration is conducted after adsorption treatment, (iii) a method in which adsorption treatment is conducted after filtration, and (iv) a method in which adsorption treatment is conducted after filtration, and filtration is further conducted. In the present invention, any of these combinations is available.

The adsorption temperature and the filtration temperature vary depending on the type of the plasticizer. However, they are generally between 30° and 120° C., preferably between 50° and 100° C. When the procedures are conducted at a temperature of lower than 30° C., the effect is decreased. When the temperature is higher than 120° C., decomposition of the plasticizer occurs, making it impossible to obtain a high volume resistivity.

In accordance with the second invention, a crude ester is produced, and finefiltration is conducted, so that a plasticizer ester having an excellent volume resistivity can easily be obtained by a simple procedure economically advantageously.

The present invention is illustrated more specifically by referring to the following Examples. However, the present invention is not limited to these Examples. In tables showing filtration conditions and results of measurement, R indicates Radiolite, and the parenthesized value indicates a ratio (% by weight) of particles having a particle size of 5 microns or less.

DESCRIPTION OF THE PREFERRED EMBODIMENTS

Example 1

2-Ethylhexyl alcohol (8,970 g, 69 mols) was subjected to deoxidation treatment at 50° C. for 30 minutes while being stirred upon previously reducing the pressure to 30 mmHG (absolute pressure). This alcohol and 4,440 g (30 mols) of phthalic anhydride were charged into a reactor which had been purged with an oxygen-free nitrogen gas. Nine grams of tetraisopropyl titanate were added thereto, and the mixture was heated at from 190° C. to 220° C. for 3 hours while being stirred to conduct a dehydro-esterification reaction. A diesterification ratio was 99.9%. The reaction solution was cooled, and 240 g of a 2-% sodium hydroxide aqueous solution were added thereto. While the mixture was stirred at from 80° to 90° C., the neutralization and the hydrolysis of the catalyst were conducted for 30 minutes. Then, 6 g of a carbon dioxide gas was blown to convert the residual alkali into a carbonate, and excess 2-ethylhexyl alcohol was completely removed and recovered through steam stripping.

One thousand grams of the thus-obtained crude ester were taken, and precoated with a glass filter 17G-4 using 6 g of Radiolite R-#100 (filter aid made by Showa Kagaku Kogyo K. K.; an amount of a filter aid having a particle size of 5 microns or less was approximately 57.7% by weight). Then, the crude ester was filtered at 50° C. over the course of 1 hour (filtration rate 4.9 liters/m² in) to produce a plasticizer ester for vinyl chloride. The resulting plasticizer was measured for a hue, an acid value and a volume resistivity according to JIS K-6751. The results are shown in Table 1.

Example 2

One thousand grams of the crude ester in Example 1 were taken, and a plasticizer was obtained in the same manner as in Example 1 using 6 g of Radiolite R-#200 (amount of a filter aid having a particle size of 5 microns or less was approximately 47.4% by weight). The results of the measurement are shown in Table 1.

Example 3

One thousand grams of the crude ester in Example 1 were taken, and a plasticizer was obtained in the same manner as in Example 1 using 6 g of Radiolite R-#800 (amount of a filter aid having a particle size of 5 microns or less was approximately 2.4% by weight). The results of the measurement are shown in Table 1.

Example 4

One thousand grams of the crude ester in Example 1 were taken, and a plasticizer was obtained in the same manner as in Example 1 using 6 g of Celite Standard Super Cell (filter aid made by Johns Manville Corp.; an amount of a filter aid having a particle size of 5 microns or less was approximately 24% by weight). The results of the measurement are shown in Table 1.

Example 5

One thousand grams of the crude ester in Example 1 were taken, and a plasticizer was obtained in the same manner as in Example 1 by simultaneously conducting adsorption and filtration using 6 g of Radiolite. R-#100 and 1 g of activated carbon. The results of the measurement are shown in Table 1.

Example 6

A plasticizer was obtained as in Example 5 except that activated carbon was replaced with 6 g of Sekado KW (alumina silica adsorbent made by Shinagawa Shirayaki Kawara K. K.). The results of the measurement are shown in Table 1.

Example 7

A plasticizer was obtained as in Example 6 except that Sekado KW was replaced with activated alumina. The results of the measurement are shown in Table 1.

Example 8

A plasticizer was obtained as in Example 7 except that activated alumina was replaced with magnesium oxide. The results of the measurement are shown in Table 1.

Example 9

One thousand grams of the crude ester in Example 1 were taken, and adsorption and filtration were then conducted simultaneously as in Example 1 using 4 g of Radiolite R-#100, 2 g of Radiolite R-#800 and 6 g of Sekado KW to obtain a plasticizer. The results of the measurement are shown in Table 1.

Example 10

One thousand grams of the crude ester in Example 1 were taken, and adsorption and filtration were then conducted simultaneously as in Example 1 using 6 g of Radiolite R-#100 and 6 g of Sekado KW to obtain a plasticizer. The results of the measurement are shown in Table 1.

Example 11

One thousand grams of the crude ester in Example 1 were taken, and a plasticizer was obtained as in Example 1 using 6 g of Sekado KW. The results of the measurement are shown in Table 1.

Example 12

2-Ethylhexyl alcohol (2,990 g, 23 mols) was previously subjected to deoxidation treatment through bubbling at room temperature for 1 hour using 100N 1/h of an oxygen-free nitrogen gas while being stirred.

A crude ester was obtained as in Example 1 using this alcohol, 1,480 g (10 mols) of phthalic anhydride and 3 g of tetraisopropyl titanate. One thousand grams of this crude ester were taken, and purified under the same conditions as in Example 1. The results of the measurement are shown in Table 1.

Example 13

One thousand grams of the crude ester in Example 12 were taken, and purified under the same conditions as in Example 5. The results of the measurement are shown in Table 1.

Comparative Example 1

A crude ester was obtained as in Example 1 except that dissolved oxygen in 2-ethylhexyl alcohol was not removed in Example 1. One thousand grams of this crude ester were taken, and purified under the same conditions as in Example 1. The results of the measurement are shown in Table 1.

Comparative Example 2

One thousand grams of the crude ester in Comparative Example 1 were taken, and purified under the same conditions as in Example 5. The results of the measurement are shown in Table 1.

Comparative Example 3

One thousand grams of the crude ester in Comparative Example 1 were taken, and purified under the same conditions as in Example 10. The results of the measurement are shown in Table 1.

TABLE 1

| | Conditions | | | | Results | | |
|---|---|---|---|---|---|---|---|
| | Alcohol deoxidation | Filter aid Adsorbent | Addition Amount g | Treatment temp. °C. | Hue APHA | Acid value mgKOH/g | Volume resistivity $\Omega \cdot cm$ at 30° C. |
| Example 1 | yes | R-#100 (57.7)[1] | 6 (4.9)[2] | 50 | 10 | 0.01 | $35 \times 10^{11}$ |
| Example 2 | yes | R-#200 (47.4) | 6 (5.0) | 50 | 10 | 0.01 | $28 \times 10^{11}$ |
| Example 3 | yes | R-#800 (2.4) | 6 (5.5) | 50 | 10 | 0.01 | $1.2 \times 10^{11}$ |
| Example 4 | yes | Celite SSC (24) | 6 (5.5) | 50 | 10 | 0.01 | $15 \times 10^{11}$ |
| Example 5 | yes | R-#100 Activated C | 6 1 | 50 | 10 | 0.01 | $35 \times 10^{11}$ |
| Example 6 | yes | R-#100 Sekado | 6 6 | 50 | 10 | 0.01 | $57 \times 10^{11}$ |
| Example 7 | yes | R-#100 Activated Al | 6 6 | 50 | 10 | 0.01 | $47 \times 10^{11}$ |
| Example 8 | yes | R-#100 Mg oxide | 6 6 | 50 | 10 | 0.01 | $43 \times 10^{11}$ |
| Example 9 | yes | R-#100 R-#800 Sekado | 4 2 6 | 50 | 10 | 0.01 | $49 \times 10^{11}$ |
| Example 10 | yes | R-#200 Sekado Activated C | 6 6 1 | 50 | 10 | 0.01 | $57 \times 10^{11}$ |
| Example 11 | yes | Sekado | 6 | 50 | 10 | 0.01 | $36 \times 10^{11}$ |

TABLE 1-continued

|  | Conditions | | | | Results | | |
| --- | --- | --- | --- | --- | --- | --- | --- |
|  | Alcohol deoxidation | Filter aid Adsorbent | Addition Amount g | Treatment temp. °C. | Hue APHA | Acid value mgKOH/ g | Volume resistivity Ω · cm at 30° C. |
| Example 12 | yes | R-#100 | 6 | 50 | 10 | 0.01 | $35 \times 10^{11}$ |
| Example 13 | yes | R-#100 Activated C | 6 1 | 50 | 5 | 0.01 | $35 \times 10^{11}$ |
| Comparative Example 1 | no | R-#100 | 6 | 50 | 30 | 0.01 | $35 \times 10^{11}$ |
| Comparative Example 2 | no | R-#100 Activated C | 6 1 | 50 | 20 | 0.01 | $35 \times 10^{11}$ |
| Comparative Example 3 | no | R-#100 Sekado Activated C | 6 6 1 | 50 | 20 | 0.01 | $57 \times 10^{11}$ |

Notes:
1) The parenthesized value under the filter aid indicates a ratio (%) of a particle size of 5 microns or less.
2) The parenthesized value under the amount indicates a filtration rate (liters/m² min).

Example 14

A crude ester was obtained as in Example 1 except that isononyl alcohol was used as an alcohol instead of 2-ethylhexyl alcohol in Example 1. One thousand grams of this crude ester were purified under the same conditions as in Example 1. The results of the measurement are shown in Table 2.

Example 15

The purification was conducted under the same conditions as in Example 3 using the crude ester obtained in Example 14. The results of the measurement are shown in Table 2.

Example 16

The purification was conducted under the same conditions as in Example 5 using the crude ester obtained in Example 14. The results of the measurement are shown in Table 2.

Example 17

The purification was conducted under the same conditions as in Example 6 using the crude ester obtained in Example 14. The results of the measurement are shown in Table 2.

Example 18

The purification was conducted under the same conditions as in Example 9 using the crude ester obtained in Example 14. The results of the measurement are shown in Table 2.

Example 19

The purification was conducted under the same conditions as in Example 10 using the crude ester obtained in Example 14. The results of the measurement are shown in Table 2.

Example 20

The purification was conducted under the same conditions as in Example 11 using the crude ester obtained in Example 14. The results of the measurement are shown in Table 2.

Example 21

A crude ester was obtained as in Example 12 except that isononyl alcohol was used instead of 2-ethylhexyl alcohol in Example 12. One thousand grams of this crude ester were purified under the same conditions as in Example 14. The results of the measurement are shown in Table 2.

Example 22

One thousand grams of the crude ester in Example 21 were taken, and purified under the same conditions as in Example 16. The results of the measurement are shown in Table 2.

Comparative Example 4

A crude ester was obtained as in Example 14 except that dissolved oxygen in isononyl alcohol was not removed in Example 14. One thousand grams of this crude ester were taken, and purified under the same conditions as in Example 14. The results of the measurement are shown in Table 1.

Comparative Example 5

One thousand grams of the crude ester in Comparative Example 4 were taken, and purified under the same conditions as in Example 17. The results of the measurement are shown in Table 2.

Comparative Example 6

One thousand grams of the crude ester in Comparative Example 4 were taken, and purified under the same conditions as in Example 19. The results of the measurement are shown in Table 2.

TABLE 2

| | Conditions | | | | Results | | |
|---|---|---|---|---|---|---|---|
| | Alcohol deoxidation | Filter aid Adsorbent | Addition Amount g | Treatment temp. °C. | Hue APHA | Acid value mgKOH/g | Volume resistivity Ω·cm at 30° C. |
| Example 14 | yes | R-#100 (57.7)[1] | 6 (4.9)[2] | 50 | 10 | 0.01 | 48 × 10$^{11}$ |
| Example 15 | yes | R-#800 (2.4) | 6 (5.3) | 50 | 10 | 0.01 | 7.8 × 10$^{11}$ |
| Example 16 | yes | R-#100 Activated C | 6 1 | 50 | 10 | 0.01 | 48 × 10$^{11}$ |
| Example 17 | yes | R-#100 Sekado | 6 6 | 50 | 10 | 0.01 | 84 × 10$^{11}$ |
| Example 18 | yes | R-#100 R-#800 Sekado | 4 2 6 | 50 | 10 | 0.01 | 65 × 10$^{11}$ |
| Example 19 | yes | R-#100 Sekado Activated C | 6 6 1 | 50 | 10 | 0.01 | 84 × 10$^{11}$ |
| Example 20 | yes | Sekado | 6 | 50 | 10 | 0.01 | 50 × 10$^{11}$ |
| Example 21 | yes | R-#100 | 6 | 50 | 10 | 0.01 | 48 × 10$^{11}$ |
| Example 22 | yes | R-#100 Activated C | 6 1 | 50 | 5 | 0.01 | 48 × 10$^{11}$ |
| Comparative Example 4 | no | R-#100 | 6 | 50 | 30 | 0.01 | 48 × 10$^{11}$ |
| Comparative Example 5 | no | R-#100 Activated C | 6 1 | 50 | 20 | 0.01 | 48 × 10$^{11}$ |
| Comparative Example 6 | no | R-#100 Sekado Activated C | 6 6 1 | 50 | 20 | 0.01 | 84 × 10$^{11}$ |

Notes:
[1] The parenthesized value under the filter aid indicates a ratio (%) of a particle size of 5 microns or less.
[2] The parenthesized value under the amount indicates a filtration rate (liters/m$^2$ min).

Example 23

A crude ester was obtained as in Example 1 except that trimellitic anhydride was used instead of phthalic anhydride in Example 1. One thousand grams of this crude ester were taken, and treated at 80° C. as in Example 1. The results of measuring the plasticizer obtained are shown in Table 3.

Example 24

The same treatment as that in Example 3 was conducted at 80° C. using the crude ester obtained in Example 23. The results of measuring the plasticizer obtained are shown in Table 3.

Example 25

The same treatment as that in Example 5 was conducted at 80° C. using the crude ester obtained in Example 23. The results of measuring the plasticizer obtained are shown in Table 3.

Example 26

The same treatment as that in Example 6 was conducted at 80° C. using the crude ester obtained in Example 23. The results of measuring the plasticizer obtained are shown in Table 3.

Example 27

The same treatment as that in Example 9 was conducted at 80° C. using the crude ester obtained in Example 23. The results of measuring the plasticizer obtained are shown in Table 3.

Example 28

The same treatment as that in Example 10 was conducted at 80° C. using the crude ester obtained in Example 23. The results of measuring the plasticizer obtained are shown in Table 3.

Example 29

The same treatment as that in Example 11 was conducted at 80° C. using the crude ester obtained in Example 23. The results of measuring the plasticizer obtained are shown in Table 3.

Comparative Example 7

A crude ester was obtained as in Example 1 except that dissolved oxygen in 2-ethylhexyl alcohol was not removed in Example 23. One thousand grams of this crude ester were taken, and purified under the same conditions as in Example 23. The results of the measurement are shown in Table 3.

Comparative Example 8

One thousand grams of the crude ester in Comparative Example 7 were taken, and subjected to the same treatment as that in Example 25. The results of the measurement are shown in Table 3.

Comparative Example 9

One thousand grams of the crude ester in Comparative Example 7 were taken, and subjected to the same treatment as that in Example 28. The results of the measurement are shown in Table 3.

TABLE 3

| | Conditions | | | | Results | | |
|---|---|---|---|---|---|---|---|
| | Alcohol deoxidation | Filter aid Adsorbent | Addition Amount g | Treatment temp. °C. | Hue APHA | Acid value mgKOH/g | Volume resistivity Ω · cm at 30° C. |
| Example 23 | yes | R-#100 (57.7)[1] | 6 (4.9)[2] | 80 | 25 | 0.04 | $52 \times 10^{11}$ |
| Example 24 | yes | R-#800 (2.4) | 6 (5.3) | 80 | 25 | 0.04 | $12 \times 10^{11}$ |
| Example 25 | yes | R-#100 Activated C | 6 1 | 80 | 20 | 0.04 | $52 \times 10^{11}$ |
| Example 26 | yes | R-#100 Sekado | 6 6 | 80 | 25 | 0.04 | $93 \times 10^{11}$ |
| Example 27 | yes | R-#100 R-#800 Sekado | 4 2 6 | 80 | 25 | 0.04 | $71 \times 10^{11}$ |
| Example 28 | yes | R-#100 Sekado Activated C | 6 6 1 | 80 | 20 | 0.04 | $93 \times 10^{11}$ |
| Example 29 | yes | Sekado | 6 | 80 | 25 | 0.04 | $54 \times 10^{11}$ |
| Comparative Example 7 | no | R-#100 | 6 | 80 | 45 | 0.04 | $52 \times 10^{11}$ |
| Comparative Example 8 | no | R-#100 Activated C | 6 1 | 80 | 35 | 0.04 | $52 \times 10^{11}$ |
| Comparative Example 9 | no | R-#100 Sekado Activated C | 6 6 1 | 80 | 35 | 0.04 | $93 \times 10^{11}$ |

Notes:
[1] The parenthesized value under the filter aid indicates a ratio (%) of a particle size of 5 microns or less.
[2] The parenthesized value under the amount indicates a filtration rate (liters/m² min).

What is claimed is:

1. A process for producing a plasticizer ester, which comprises previously removing dissolved oxygen in a starting alcohol, and then subjecting an organic acid or its anhydride and the alcohol to an esterification reaction in the presence of an organic metal compound catalyst.

2. The process for producing the plasticizer ester according to claim 1, wherein the removal of dissolved oxygen in the starting alcohol is conducted at a temperature of from 30° to 100° C.

3. The process for producing the plasticizer ester according to claim 1, which comprises adding an alkaline aqueous solution to the reaction product obtained by the esterification reaction to conduct neutralization of an unreacted acid and hydrolysis of the catalyst, further blowing a carbon dioxide gas to convert the residual alkali into a carbonate, recovering an excess alcohol, and then conducting purification through finefiltration and/or adsorption treatment.

4. A process for producing a plasticizer ester, which comprises subjecting an organic acid or its anhydride and an alcohol to an esterification reaction in the presence of an organic metal compound catalyst, adding an alkaline aqueous solution to the reaction product obtained to conduct neutralization of an unreacted acid and hydrolysis of the catalyst, blowing a carbon dioxide gas to convert the residual alkali into a carbonate, recovering an excess alcohol, and then conducting finefiltration using a filter aid.

5. The process for producing the plasticizer ester according to claim 4, which comprises subjecting an organic acid or its anhydride and an alcohol to an esterification reaction in the presence of an organic metal compound catalyst, adding an alkaline aqueous solution to the reaction product obtained to conduct neutralization of an unreacted acid and hydrolysis of the catalyst, blowing a carbon dioxide gas to convert the residual alkali into a carbonate, recovering an excess alcohol, and then conducting purification through finefiltration and adsorption treatment.

6. The process for producing the plasticizer ester according to claim 4 or 5, wherein the finefiltration is conducted using a filter aid in which a filter aid having a particle size of 5 microns or less occupies 20% by weight or more of the total weight.

7. The process for producing the plasticizer ester according to claim 6, wherein a filter aid having a particle size of 5 microns or less occupies 30% by weight or more of the total weight.

8. The process for producing the plasticizer ester according to claim 5, wherein the amount of the filter aid is between 1 and 5 kg per m² of the filtration area.

9. The process for producing the plasticizer ester according to claim 4 or 5, wherein the filtration rate is 10 liters/min per m² or less of the filtration area.

10. The process for producing the plasticizer ester according to claim 5, wherein the amount of the adsorbent is between 0.1 and 1% by weight based on the weight of the crude ester.

11. The process for producing the plasticizer ester according to claim 5, wherein the temperature of the adsorption treatment and the filtration is between 30° and 120° C.

* * * * *